(12) United States Patent
Chen et al.

(10) Patent No.: US 11,098,380 B2
(45) Date of Patent: Aug. 24, 2021

(54) REAGENT AND METHOD FOR RAPID DETECTION OF PORCINE ADENOVIRUS

(71) Applicant: JIAXING ANYU BIOTECHNOLOGY CO., LTD., Zhejiang (CN)

(72) Inventors: Ping Chen, Zhejiang (CN); Na Li, Zhejiang (CN); Xintao Zhong, Zhejiang (CN); Tingting Zhang, Zhejiang (CN); Nan Li, Zhejiang (CN)

(73) Assignee: JIAXING ANYU BIOTECHNOLOGY CO., LTD., Jiaxing (CN)

( * ) Notice: Subject to any disclaimer, the term of this patent is extended or adjusted under 35 U.S.C. 154(b) by 236 days.

(21) Appl. No.: 16/173,610

(22) Filed: Oct. 29, 2018

(65) Prior Publication Data
US 2019/0127811 A1 May 2, 2019

(30) Foreign Application Priority Data

Oct. 30, 2017 (CN) .......................... 201711030142.2

(51) Int. Cl.
*C12Q 1/68* (2018.01)
*C12Q 1/70* (2006.01)

(52) U.S. Cl.
CPC ......... *C12Q 1/701* (2013.01); *C12Q 2600/16* (2013.01)

(58) Field of Classification Search
None
See application file for complete search history.

(56) References Cited

U.S. PATENT DOCUMENTS

2010/0083391 A1* 4/2010 Hamilton ........... A01K 67/0271
800/10

OTHER PUBLICATIONS

Nagy et al. (J Gen Virology, 2001, 82:525-529) (Year: 2001).*
Lowe et al. (Nucleic Acids Research, 1990, 18(7):1757-1761) (Year: 1990).*
Segales et al. (Veterinary Microbiology 2005, 111, p. 223-229) (Year: 2005).*
Larocque et al. (2016, AB026117.1 database entry, obtained from NCBI) (Year: 2016).*

* cited by examiner

*Primary Examiner* — Stephanie K Mummert
(74) *Attorney, Agent, or Firm* — NZ Carr Law Office

(57) ABSTRACT

The invention provides are agent and a method using this reagent for the detection of porcine adenovirus in a sample. The reagent comprises the following primer pair: the upstream primer: (5'-3') ATCTTGAAATCACAATTCTTCTG (SEQ ID NO: 1); the downstream primer: (5'-3') CAAGGAGCAGYTGGTGGAG (SEQ ID NO: 2), among the downstream primer Y can be T or C. This reagent and method are of strong specificity and high sensitivity, which can rapidly detect pig porcine adenovirus in samples.

4 Claims, 3 Drawing Sheets

Specification includes a Sequence Listing.

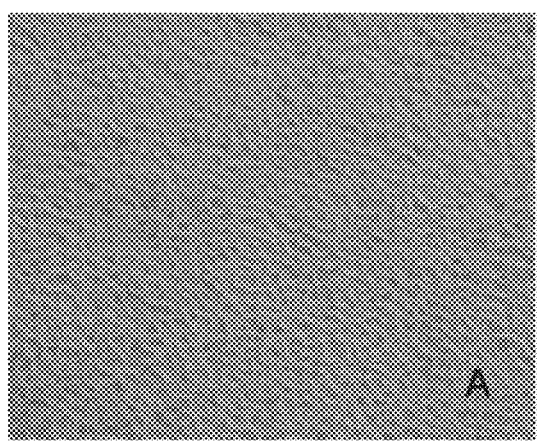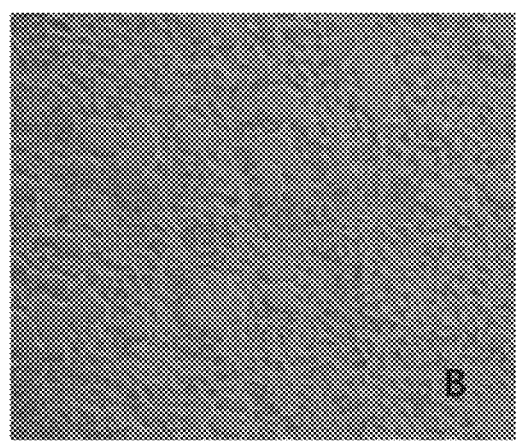
Figure 1A                    Figure 1B
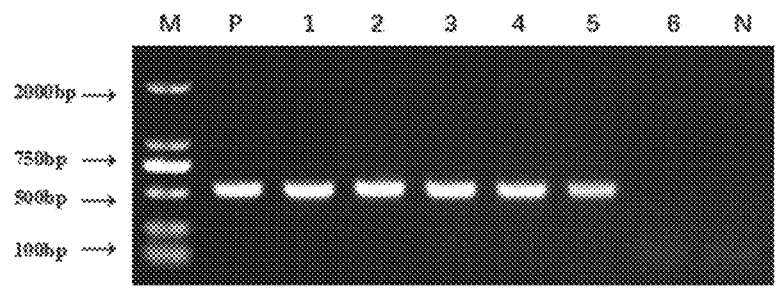
Figure 2
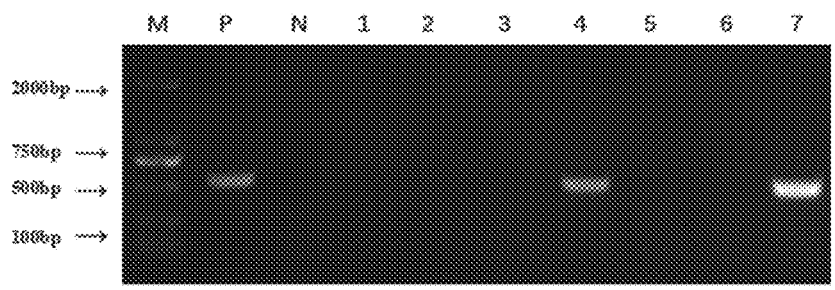
Figure 3
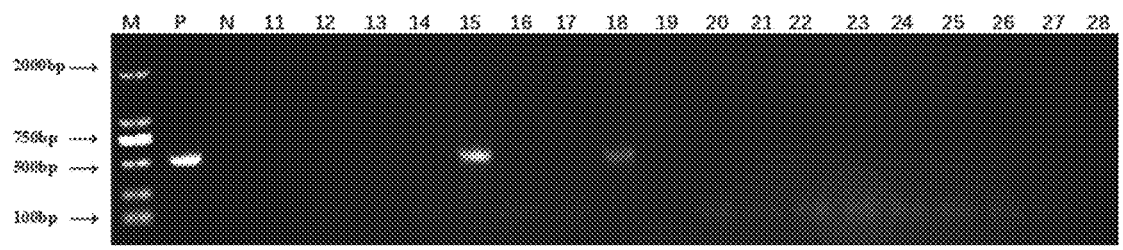
Figure 4

REAGENT AND METHOD FOR RAPID DETECTION OF PORCINE ADENOVIRUS

RELATED APPLICATION

This application claims priority to Chinese Application Serial No. 201711030142.2, filed Oct. 30, 2017, which is herein incorporated by reference in its entirety.

SEQUENCE LISTING

This application is accompanied by a sequence listing both on paper and in a computer readable form that accurately reproduces the sequences described herein.

FIELD OF THE INVENTION

The present invention relates to a reagent and method for detecting adenovirus in a fluid sample, specifically, a reagent and a method for rapid and effective detection of swine adenovirus.

BACKGROUND OF THE INVENTION

The following background techniques, which could not deem as the existing technology, are introduced to help the readers for understanding the present invention.

Adenovirus is a kind of double-stranded DNA virus with a typical icosahedron virus shell. Its shell contains three main viral proteins, namely six neighbors, five neighboring and fiber, play an important role in infections. In adenovirus infection, the early replication of genes mainly included E1A, E1B, E2A, E2B, E3 and E4. Among them, the expression product of E1 gene is an indispensable for viral replication, and plays an important role in the replication and transformation of protein.

Swine adenovirus belongs to the adenovirus family in Mammalian adenovirus. This kind of virus has 4 serotypes, and can cause some clinical symptoms such as encephalitis, nephritis, pneumonia and diarrhea. It exists in a common pig herd and can be detected in the nasal cavity, anus and feces of pigs. According to the results from the virus isolation and antibody detection, it was found that all the pigs in the world are suffering from the infection of the adenovirus.

Porcine adenovirus only infects pigs and does not infect humans and other animals. However this virus can transduce a variety of human and animal cells. With the high proliferation of pig-adenovirus vectors, the exogenous gene can be carried stably and expressed efficiently in transducing cells. At the same time, there is no cross—immune response between the pig adenovirus and human adenovirus. Therefore, the porcine adenoviral vector can be used as a delivery system for swine vaccines, and it also has potential to be used for human gene therapy and vaccine delivery system. At present, the work on the study of vaccine carrier of pig adenovirus is much less than that of human adenovirus. The porcine adenovirus vector vaccine will be an important part for the development of the vaccine vector development. Meantime, the detection of porcine adenovirus is also a shortcoming of its marketization.

The application of animal vaccine based on replication defective adenovirus vector in animal husbandry is being carried out on a large scale. According to strict regulations on the safety of transgenic technology, the safety and environmental impact of replication-defective adenoviral vector vaccines in pigs and cattle need to be rapidly detected. At present, porcine adenovirus, bovine adenovirus, and human replication-defective adenovirus have become the types of adenovirus most concerned in animal husbandry production, the demand for the rapid detection of identification has a broad and great prospect. The above three adenoviruses are prone to diverse infection. Thus, rapid detection and identification are very difficult.

Currently, cell culture method, adsorption method, blood immune of fluorescence test are widely used in biological products industry, but these methods are of low sensitivity, long time consuming, and low detection precision. Moreover, the results are susceptible to a variety of factors, such as, lack of objectivity and strenuosity, etc. Although the conventional PCR detection method is sensitive, stable and specific, it is easy to be contaminated to cause false positive results. Therefore, it's needed to provide a more reliable reagent and method for the rapid detection of adenovirus, particularly porcine adenovirus.

SUMMARY OF THE INVENTION

In the present invention, the on-line BLAST was used to find the highly conserved region DNA sequence DBP (DNA Binding Protein) of the porcine adenovirus according to the reported porcine adenovirus gene sequence in the NCBI database. The highly conserved region DNA sequence DBP which is highly homologous in different kinds of serotype. The universal primers which can be used for detection of the sequence specifically have been designed after repeated comparison and sifting, and they can not only be used for detection of porcine adenovirus type 5, but also can be used for detection of the other three known serotypes.

In one aspect, the invention provides an agent for detecting porcine adenovirus, where in the reagent comprises a pair of primers.

The upstream primer (5'-3'): ATCTTGAAATCACAAT-TCTTCTG (SEQ ID NO: 1). The downstream primer (5'-3'): CAAGGAGCAGYTGGTGGAG (SEQ ID NO: 2), Y can be T or C.

In some preferred embodiments, the reagent includes a necessary component that is capable of performing nucleic acid amplification. In some preferred ways, the necessary reagent includes Taq DNA polymerase.

In some preferred embodiments, the nucleic acid amplification method can be one or several kinds of method such as PCR, Recombinase Polymerase Amplification (RPA), transcription mediated amplification, nucleic acid sequence-based amplification, signal mediated RNA amplification technology, Strand Displacement Amplification, Rolling Circle Amplification, Loop-Mediated DNA Isothermal Amplification, Isothermal Multiplex Amplification, Helicase-dependent Amplification, Single Primer Isothermal Amplification, Cyclic-Helicase-Independent Amplification, and Isolation And extend amplification reactions.

In another aspect, the present invention relates to the use of a primer sequence for the preparation of reagent that can be used for detection of a porcine adenovirus in a test sample The upstream primer (5'-3'): ATCTTGAAATCACAAT-TCTTCTG (SEQ ID NO: 1). The downstream primer (5'-3'): CAAGGAGCAGYTGGTGGAG (SEQ ID NO: 2), Y can be T or C.

In all of the foregoing methods or uses, the porcine adenovirus includes porcine adenovirus type 5.

In all of the foregoing methods or uses, the porcine adenovirus includes porcine adenovirus type AB026117.1, AC_000009.1, AF289262.1 or AJ237815.1. The samples are collected from the pig's nasal cavity, or anus.

In another aspect, the invention provides a method for detecting porcine adenovirus, including PCR. The PCR amplification conditions are as follows: pre-denaturation at 95° C. for 5 min, denaturation at 95° C. for 30 s, annealing at 60° C. for 30 s, elongation at 72° C. for 30 s, and final extension at 72° C. for 7 min after 35 cycles.

In some preferred embodiments, the method also provides a reaction mixture consists of 3 ul of sample DNA, 1 ul of 10 uM upstream primer, 1 ul of 10 uM downstream primer, 25 ul of Taq DNA polymerase, 20 ul of ultrapure water.

The upstream primer (5'-3'): ATCTTGAAATCACAAT-TCTTCTG (SEQ ID NO: 1). The downstream primer (5'-3'): CAAGGAGCAGYTGGTGGAG (SEQ ID NO: 2), Y is T.

Effect

The main advantages of the invention are as following: the specific primers cover a broad range of porcine adenovirus serotypes, and they can be used to distinguish adenoviruses of different animals and can avoid the false negative results caused by the non-specific binding of multiple pairs of primers in multiplex PCR. The detection period is quite short, which is very suitable for the identification of a large number of clinical samples, and can greatly reduce the test period of animal experiments. Compared with the prior method, the amplified fragment of the invention is located in the DNA Binding protein (DBP) region of the adenovirus and which is a relatively conserved region. Specific primers can find homologous regions. At the same time, there is no cross reaction with other animal viruses such as influenza virus and foot-and-mouth disease virus. The universal primers are used in the invention, which is simple in operation and less in consumables, and can greatly reduce the operating cost, and is particularly suitable for the rapid detection of a large number of clinical samples of adenovirus infection and safety testing of transgenic technology.

Good specificity: The method is used to detect some common virus, such as Bovine adenovirus, human adenovirus, Newcastle disease virus and influenza A virus. All the results were shown as negative indicating that the method relates to the present invention has good specificity.

High accuracy: The result of porcine adenovirus isolation is consistent with the results of sequencing, and it is applicable to samples with different sampling locations and sampling times.

High sensitivity: it also works for ten-fold dilution of positive samples for PCR amplification.

BRIEF DESCRIPTION OF THE DRAWINGS

FIGS. 1A and 1B show the result of A-293 cells infected by a swab sample. A: Normal A-293 cells B: Pathological A-293 cells.

FIG. 2 shows the result of PCR amplification of virus DNA of diseased cells. M: marker; P: positive control (porcine adenovirus type 5); 1-5: viral DNA of pathological cell; 6: viral DNA of undiseased cell; N: negative control.

FIG. 3 shows the PCR amplification of virus DNA from swab samples, M: marker; P: positive control (porcine adenovirus type 5); N: negative control; 1 to 7: virus DNA from swab samples.

FIG. 4 shows PCR amplification of virus DNA from swab samples, where M: marker; P: positive control (porcine adenovirus type 5); N: negative control; 11 to 28: viral DNA from swab samples.

DETAILED DESCRIPTION

Figure 5:
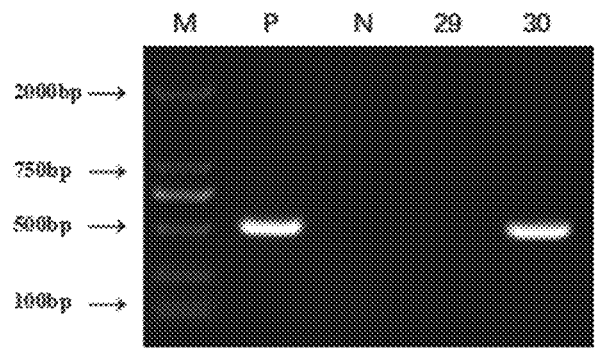
FIG. 5 shows PCR amplification of virus DNA from swab samples, where M: marker; P: positive control (porcine adenovirus type 5); N: negative control; 11 to 28: viral DNA from swab samples.

The following descriptions will serve to further illustrate the invention but are not intended to be a limitation on the scope of the invention.

Detection

Detection means testing the presence of a substance or material, such as, but not limited to, chemical substances, organic compounds, inorganic compounds, metabolites, drugs or drug metabolites, metabolites of organic or organic tissues, nucleic acids, Protein or polymer. In addition, the detection includes the detection of the amount of the substance or material. Further, the detection also includes immunological tests, chemical tests, enzyme tests, etc.

Samples

Samples that can be tested with the device of the present invention include liquids of biological origin (e.g., casing fluids and clinical samples). Liquid or fluid samples can be derived from solid or semi-solid samples, including excreta, biological tissue, and food samples. The solid or semi-solid sample can be converted to a liquid sample using any suitable method, such as mixing, mashing, macerating, incubating, dissolving, or using an enzyme digesting solid samples in a suitable solution (e.g., water, phosphate solution, or other buffered solution). "Biological specimens" include samples derived from animals, plants and foodstuffs, including, for example, human or animal derived urine, saliva, blood and its components, spinal fluid, vaginal secretions, sperm, feces, sweat, secretions, tissues, organs, tumors, tissue and organ cultures, cell cultures and media. Preferably the biological sample is urine or a swab. Food samples include food processed substances, and products, meat, cheese, wine, milk and drinking water. Plant samples include any plant, plant tissue, plant cell culture and medium. "Environmental samples" are derived from the environment (for example, liquid samples from lakes or other bodies of water, sewage samples, soil samples, groundwater, seawater, and waste samples). Environmental samples may also include sewage or other waste water. With the present invention and suitable detection elements, any analyte can be detected.

It is preferred to use the present invention to detect adenoviruses in swabs, and in particular, to detect adenoviruses in swine swabs, which can collect samples from the nasal cavity, the anus, or other sites.

Nucleic Acid Detection Methods

The detection method of the present invention may be any method for amplifying a nucleic acid, such as PCR, or other amplification methods, such as various nucleic acid amplification techniques, including Recombinase Polymerase Amplification (RPA), transcription mediated amplification, nucleic acid sequence-based amplification, signal mediated RNA amplification technology, Strand Displacement Amplification, Rolling Circle Amplification, Loop-Mediated DNA Isothermal Amplification, Isothermal Multiplex Amplification, Helicase-dependent Amplification, Single Primer Isothermal Amplification, Cyclic-Helicase-Independent Amplification, and Isolation And extend amplification reactions (refer to US 2009/0017453). Polymerase chain reaction is the most widely known method, but the difference is that it requires the use of thermal cycling to cause nucleic acid strand separation. This amplification method and other amplification methods are introduced as below: Vainness et al., PNAS 2003, 100, 4504-4509; Tan et al., Anal. Chem. 2005, 77, 7984-7992; Lizard et al., Nature Biotech 1998, 6, 1197-1202; Notomi et al., NAR 2000, 28, 12, e63; Kurn et al., Clin. Chem. 2005, 51:10, 1973-1981. Additional references for these common amplification techniques, including U.S. Pat. Nos. 7,112,423, 5,455,166, 5,712,124, 5,744,311, 5,916,779, 5,556,751, 5,733,733, 5,834,202, 5,354,668, 5,591,609, 5,614,389, 5,942,391, and U.S. Patent Publication NO. US20030082590, NO. US20030138800, NO. US20040058378, NO. US20060154286. All of the above documents are incorporated herein by reference.

RPA is an exemplary isothermal nucleic acid amplification method. RPA employs an enzyme named recombinase that is capable of pairing an oligonucleotide primer with a homologous sequence in a double helix DNA. In this way, DNA synthesis involves a defined point in the sample DNA. If a target sequence is present, an exponential amplification reaction is started using two gene-specific primers. The reaction progressed rapidly and was specifically amplified from several target copies to detectable levels within 20 to 40 minutes. The RPA method is revealed in U.S. Pat. Nos. 7,270,981, 7,399,590, 7,777,958, 7,435,561, US 2009/0029421, and PCT/US2010/037611. All of the above documents are incorporated herein by reference.

Detailed Operation

In order to describe the reagents and methods of the present invention in more detail, they will now be illustrated by way of examples. These descriptions merely demonstrate how the essence of the present invention is implemented, but do not limit the scope of the claims of the present invention.

1 Material and Methods
1.1 Material
1.1.1 Samples and Cells

The specimens were from swine nasal swabs and anal swabs collected in Beijing and Henan in 2016 and 2017. The AY-293 cell lines used in the research and development were independently constructed and preserved by HEK293 cells.

1.1.2 Chemicals
DMEM culture (Gibco, 1830673)
Taq DNA polymerase (TaKaRa, A3901A)
TaKaRa MiniBEST Viral RNA/DNA Extraction Kit (TaKaRa, AK2623D)
DL 2,000 DNA Marker (TaKaRa, A2001B)
Animal tissue/cell genomic DNA extraction kit (Solar bio, 20150608)
Tissue lysate (Biomed, 706368BJ)
1.1.3 Instruments
Veriti™ 96-Well Thermal Cycler (Thermo Fisher)
Eppendorf Centrifuge 5810R (Eppendorf)
3110 Water-Jacketed CO2 Incubators (Thermo Fisher)
DK-8D constant temperature water baths (Shanghai Jinghong)
ChemiDoc™ XRS+ System (BIO-RAD)
1.2 Method
1.2.1 Clinical Monitoring and Sampling Arranging and registering the samples from various places at various times. 1 mL of PBS solution was added to per samples, and mixing them by vortex and placing the samples in a refrigerator at 4° C. for 1 hour.

1.2.2 Cell Culture

Day 1, the AY-293 cells were seeded at a cell density $2.5*10^5$ cell, amount of 0.5 mL per well in 24 well plates, followed by incubation at 37° C. with $CO_2$ concentration at 5%. Day 2, Prepare a 96-well plate with 0.1 mL per well of 5 mL DMEM which contain 0.5 mL Streptomycin. Centrifuging the swab at 2000 rmp for 10 min in 4° C., and filtrating with 0.22-micron membrane. The supernatant was added to each well in a volume of 0.1 mL in 96-well plates.

Remove the supernatant from the 24-well plate, and washing the cell with PBS solution. 0.2 mL of samples was added to the 24-well plate, followed by incubation at 37° C. for 1 h with $CO_2$ concentration at 5%. And then the supernatant were removed, and 0.5 mL DMEM which contain 5% FBS was added to the 24-well plate, followed by incubation at 37° C. for 3 days with $CO_2$ concentration at 5%. Observe continuously for 3 days to see if there is any lesion. Day 4, the AY-293 cells were seeded at a cell density $2.5*10^5$ cell, amount of 0.5 mL per well in 24 well plates, followed by incubation at 37° C. with $CO_2$ concentration at 5%. Day 5, Inoculation according to the method mentioned above after repeated freezing and thawing for 3 times at −20~30° C., and blind pass for 5 generations. Observe the condition of cytopathic effect (CPE) and collect viral fluid when the lesion reaches to 80%.

1.2.3 Viral DNA/RNA Extraction

The viral DNA from the swab sample was extracted according to the instructions using the TaKaRa MiniBEST Viral RNA/DNA Extraction Kit. The viral DNA from normal and diseased cells was extracted using animal tissue/cell genomic DNA extraction kit.

1.2.4 Primer Design

The sequence of the DNA Binding Protein (DBP) of the four serotype of Porcine Adenovirus was downloaded in the NCBI GenBank database. The gene sequence numbers for the four porcine adenovirus serotypes are AB026117.1, AC_000009.1, AF289262.1 and AJ237815.1, respectively. The homology analysis was performed, and the primer sequences was designed according to the conserved region from the respective sequences of the four serotype porcine adenoviruses. Upstream primer: (5'-3') ATCTTGAAAT-CACAATTCTTCTG (SEQ ID NO: 1); Downstream primer: (5'-3') CAAGGAGCAGYTGGTGGAG (SEQ ID NO: 2), herein, Y is T or C; The length of the amplified fragment was 534 bp.

1.2.5 PCR Amplification

A-293 cells infected with virus were collected and centrifuged at 12000 rpm for 1 min. The viral DNA was extracted using animal tissue/cell genomic DNA extraction kit. PCR amplification was performed according to the following amplification conditions.

Pre-denaturation at 95° C. for 5 min, denaturation at 95° C. for 30 s, annealing at 60° C. for 30 s, elongation at 72° C. for 30 s, 35 cycles, final elongation at 72° C. for 7 min; The positive control for each PCR amplification was porcine type 5 adenovirus and the negative control was $ddH_2O$. The PCR product was electrophoresed on 1% agarose gel and observed in a gel imaging system. The amplified PCR product was purified and recovered using a gel recovery kit and was commissioned to Invitrogen (Shanghai) Trading Co., Ltd. for sequence determination.

1.2.6 Homology Analysis

The sequencing results were assembled by using SeqMan2.0, and analyzed by BLAST with homologous sequences alignment, and then construct the evolutionary tree based on the MEGA5.0 analysis.

1.2.7 Primer Sensitivity Detection

The positive sample DNA was diluted ten-fold with dilutions of 10, $10^2$, $10^3$, $10^4$, and $10^5$ as templates and tested using the above PCR amplification system and amplification conditions.

1.2.8 Primer Specificity Analysis

Other common viruses such as influenza A virus, bovine adenovirus, human adenovirus, and Newcastle disease virus were detected using the above mentioned methods.

2 Result 2.1 Detection of Porcine Adenovirus 2.1.1 Viral Isolation

The swabs with collected samples were inoculated with A-293 cells. Under ordinary light microscope, the medium of A-293 cells without swab samples was clear and the cells were polygonal and rhomboid. However, the A-293 cells with swab samples were swollen, circles, clusters, like grapes (FIG. 2B). The results showed that 5 of the 30 collected samples are positive containing swine adenovirus 2.1.2 Virus DNA PCR Amplification and Electrophoresis Results The virus DNA of cells infected by swine adenovirus were extracted by animal tissue/cell genomic DNA extraction kit and amplified by PCR (the reagents and methods used for amplification and the reagents and methods listed in 1.2.5). The results showed that both samples of the lesioned cells gave positive results (FIG. 2).

2.2 Swab Sample Viral DNA PCR Amplification and Electrophoresis Results

The swab samples were directly extracted and detected by PCR amplification (The reagents and methods used for amplification are the same as those listed in 1.2.5.). Five of the 30 swab samples were positive; they were 4, 7, 15, 18, and 29, respectively. The results were corresponding with the results of the isolation and purification of the cells (results are shown in FIG. 3, FIG. 4 and FIG. 5).

2.3 Sequencing Results

Five target bands were sequenced separately and spliced using SeqMan 2.0. The sequencing results showed that the five target fragments were all sequenced as follows:

(SEQ ID NO: 3)
TTTGCAGCACTGAACACGAGCACCGCTGGGTGGTCCAGAGTGGCTAAAAT

CTTCGGGTCGTCCATCAGGTTTCTGTCGATGTTGCCCGGCGTAGACATGG

CAAACGGGGTCACCTTGCACGTTTGCTTGCCAAGAAGCGGCAGGTGGTTG

GCTCCCTAGTTGCACTCGCAGACCAGAGGCATGAGGAGGTGAGACTCGGC

-continued
CGTTGTCATGTTGGGATAGATGGCCGTGACGAAGGCGGCGATCTGGCGAA

AAGCGGTGACAGCTTTTGGTCCGTCAGAGTAAAAATAGCCGCAAGACTGA

GGACTGAAGGTATTGATGGGCGATTTTGCGTCGTTTACGCAGCACATGGC

GTCGCTGTTGCGGATTTGCACCACACTGCGTCCCCATCTGTTGGTGACAA

TCTTGGCCTTCTCTGGGGTTTCCTTGAGAGCTCTCTGCCCGTTTTCGCTG

TTGATATCCATCTCCACCACTGGCTCCCTGGA 2.4 Genotyping Analysis

The sequencing results were homologous compared with the U.S. National Institute of Health (NIH) BLAST program. The result was 97% homologous to porcine adenovirus type 5 (its sequence number is AF289262.1).

Figure 6:
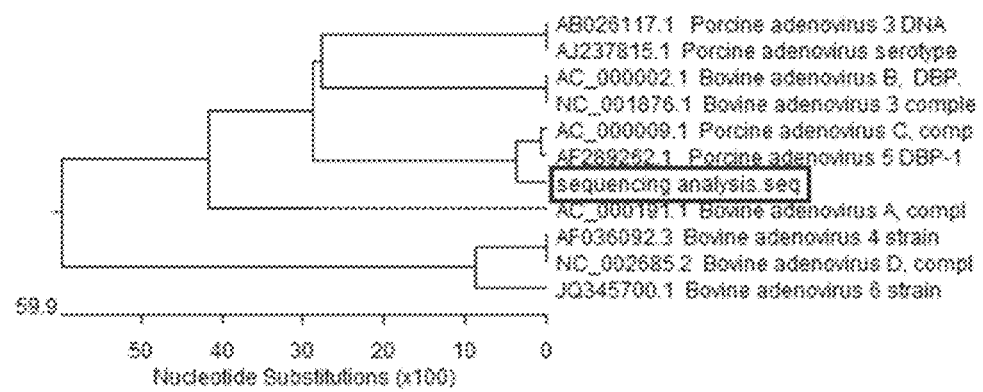
FIG. 6 shows the phylogenetic tree of the DNA Binding protein gene, where sequencing analysis is the sequencing result of the virus.

At the same time, in order to further confirm its serotype, the four serotypes of porcine adenovirus and the serotype of bovine adenovirus with serial number AC_000002.1, AC_000191.1, JQ345700.1, NC_001876.1 and NC_002685.2 were used to build the evolutionary tree by MEGA5.0 (FIG. 6). The result showed that the adenovirus was highly homologous to porcine type 5 adenovirus, and further proved that this strain was pig type 5 adenovirus (FIG. 6).

2.5 Primer Specificity Analysis

The above primers were used to detect type A influenza virus, bovine adenovirus, human adenovirus, Newcastle disease virus, and pig tissue samples (negative). No banding was observed, indicating that the primers had good specificity without cross-reactions.

Figure 7:
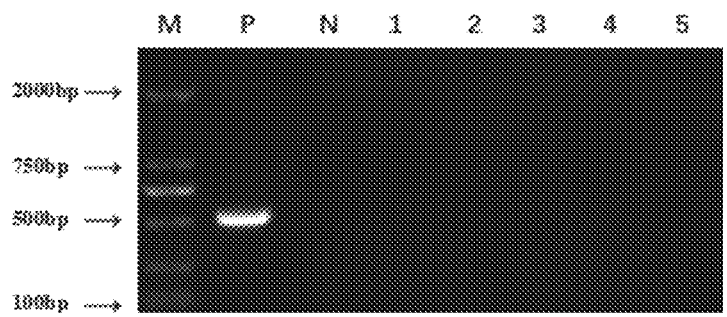
FIG. 7 shows the results of primer-specific detection, M: marker; P: positive control (porcine adenovirus type 5); N: negative control; 1: influenza virus type A; 2: bovine adenovirus; 3: human adenovirus; 4: Newcastle disease virus; 5: Pig tissue sample.
Figure 8:
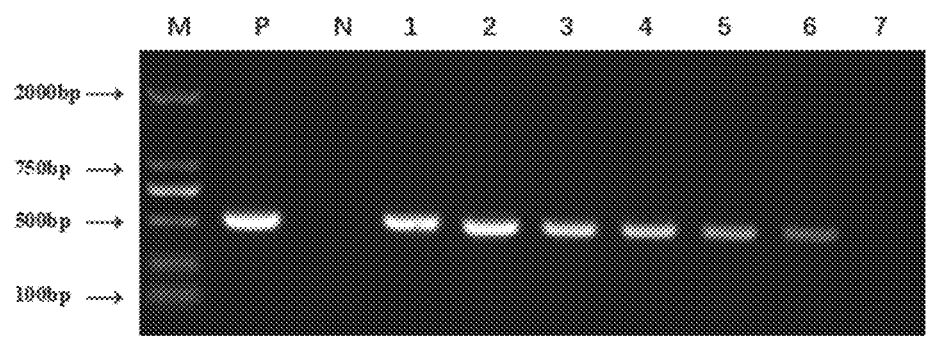
FIG. 8 shows the results of primer-specific detection, M: marker; P: positive control (porcine adenovirus type 5); N: negative control; 1-7: the template DNA with dilutions of 10, $10^2$, $10^3$, $10^4$, $10^5$, $10^6$ and $10^7$, respectively (left to right).

The primer pair used was as follows:

The upstream primer was: (5'-3') ATCTTGAAAT-CACAATTCTTCTG (SEQ ID NO: 1); the downstream primer was CAAGGAGCAGYTGGTGGAG (SEQ ID NO: 2), where Y is T. Alternatively, the upstream primer is: (5'-3') ATCTTGAAATCACAATTCTTCTG (SEQ ID NO: 1); the downstream primer is CAAGGAGCAGYTGGTGGAG (SEQ ID NO: 2), where Y is C. All results obtained as shown in FIG. 7, it indicated that the primer pair has high specificity.

At the same time, when parallel primers are used, for example, Y is A or G in the downstream primer, the result are positive both with bovine adenovirus and human adenovirus. This indicated that when Y in the downstream primer is A or G, the primer does not have specificity and cannot be used to distinguish specific species of viruses (FIG. 7).

2.6 Primer Sensitivity Analysis

The positive sample DNA was diluted ten-fold with dilutions of 10, $10^2$, $10^3$, $10^4$, $10^5$, $10^6$, and $10^7$. The minimum dilution for PCR amplification was 106, indicating that the specific primers of the present invention have a high sensitivity (FIG. 7).

2.7 Result Statistics

TABLE 1

PCR detection of Swab samples and the virus isolation results statistics.

| species | sample name | Sampling location | sampling time | Number of samples | PCR test results | Sequencing results | Virus isolation results |
|---|---|---|---|---|---|---|---|
| swine | Anal swab | Henan | 2016 Nov. 25 | 3 | 0 | 0 | 0 |
| swine | nose swabs | Henan | 2016 Nov. 25 | 3 | 1/3 | 1/3 | 1/3 |
| swine | Anal swab | Beijing | 2017 Mar. 7 | 4 | 2/3 | 2/3 | 2/3 |
| swine | nose swabs | Beijing | 2017 Mar. 7 | 4 | 0 | 0 | 0 |
| bovine | Anal swab | Beijing | 2017 Mar. 7 | 2 | 0 | 0 | 0 |
| bovine | nose swabs | Beijing | 2017 Mar. 7 | 2 | 0 | 0 | 0 |

TABLE 1-continued

PCR detection of Swab samples and the virus isolation results statistics.

| species | sample name | Sampling location | sampling time | Number of samples | PCR test results | Sequencing results | Virus isolation results |
|---|---|---|---|---|---|---|---|
| swine | Anal swab | Beijing | 2017 Aug. 15 | 4 | 1/3 | 1/3 | 1/3 |
| swine | nose swabs | Beijing | 2017 Aug. 15 | 4 | 0 | 0 | 0 |
| sow | Anal swab | Beijing | 2017 Aug. 15 | 2 | 1/2 | 1/2 | 1/2 |
| sow | nose swabs | Beijing | 2017 Aug. 15 | 2 | 0 | 0 | 0 |

The above primers obtained positive results with the two primer pairs of the present invention, which are consistent with the results of cell culture.

In the absence of any element or limitation specifically disclosed herein, the invention illustrated and described herein may be practiced. The terms and expressions employed are used as terms of description and not of limitation, and it is not intended to exclude any equivalents of the features shown and described or portions thereof in the use of these terms and expressions, and it should be recognized that each Modification are possible within the scope of the present invention. It should be understood, therefore, that although the present invention has been specifically disclosed through various embodiments and alternative features, modifications and variations of the concepts described herein can be adopted by one of ordinary skill in the art, and it is believed that these modifications and variations fall within the scope of the present invention. It is within the scope of the invention as defined in the appended claims.

The contents of articles, patents, patent applications, and all other documents and electronically available information described or documented herein are hereby incorporated by reference in their entireties to the same extent as if each individual publication was specifically Separately pointed out for reference. The applicant reserves the right to incorporate any and all materials and information from any such articles, patents, patent applications or other documents in this application.

The invention claimed is:

1. A reagent for detecting porcine adenovirus in a sample, wherein the reagent comprises the following primer pairs, wherein the the upstream primer is: (5'-3') ATCTTGAAAT-CACAATTCTTCTG (SEQ ID NO:1); and the downstream primer is (5'-3') CAAGGAGCAGYTGGTGGAG (SEQ ID NO:2), wherein Y is T or C; and wherein the porcine adenovirus is the type 5 porcine adenovirus.

2. The reagent according to claim 1, wherein the reagent includes a necessary component that is capable of performing nucleic acid amplification and the necessary component includes the Taq DNA polymerase.

3. The reagent according to claim 1, wherein the porcine adenovirus includes at least one serotype selected from the group consisting of AB026117.1, AC_000009.1, AF289262.1, and AJ237815.1.

4. The reagent according to claim 1, wherein the sample is collected in a pig's nasal cavity or anus.

* * * * *

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
atcttgaaat cacaattctt ctg                                            23

<210> SEQ ID NO 2
<211> LENGTH: 19
<212> TYPE: DNA
<213> ORGANISM: Artificial Sequence
<220> FEATURE:
<223> OTHER INFORMATION: Primer

<400> SEQUENCE: 2
caaggagcag ytggtggag                                                 19

<210> SEQ ID NO 3
<211> LENGTH: 482
<212> TYPE: DNA
<213> ORGANISM: Adenovirus

<400> SEQUENCE: 3
tttgcagcac tgaacacgag caccgctggg tggtccagag tggctaaaat cttcgggtcg    60
tccatcaggt ttctgtcgat gttgcccggc gtagacatgg caaacggggt caccttgcac   120
gtttgcttgc caagaagcgg caggtggttg gctccctagt tgcactcgca gaccagaggc   180
atgaggaggt gagactcggc cgttgtcatg ttgggataga tggccgtgac gaaggcggcg   240
atctggcgaa aagcggtgac agcttttggt ccgtcagagt aaaaatagcc gcaagactga   300
ggactgaagg tattgatggg cgattttgcg tcgtttacg agcacatggc gtcgctgttg    360
```

```
cggatttgca ccacactgcg tccccatctg ttggtgacaa tcttggcctt ctctggggtt    420
tccttgagag ctctctgccc gttttcgctg ttgatatcca tctccaccac tggctccctg    480
ga                                                                   482
```